(12) United States Patent
Miller et al.

(10) Patent No.: US 8,265,960 B2
(45) Date of Patent: Sep. 11, 2012

(54) SYSTEM AND METHOD FOR DISEASE STATE MARKETING

(75) Inventors: Amylu Miller, Wauconda, IL (US); Parag Patel, Skokie, IL (US)

(73) Assignee: Walgreen Co., Deerfield, IL (US)

( * ) Notice: Subject to any disclaimer, the term of this patent is extended or adjusted under 35 U.S.C. 154(b) by 296 days.

(21) Appl. No.: 12/709,743

(22) Filed: Feb. 22, 2010

(65) Prior Publication Data

US 2011/0125529 A1    May 26, 2011

Related U.S. Application Data

(60) Provisional application No. 61/264,040, filed on Nov. 24, 2009.

(51) Int. Cl.
    *G06Q 50/00*      (2012.01)
    *G06Q 30/00*      (2012.01)
    *G06F 15/16*      (2006.01)

(52) U.S. Cl. .............................. 705/3; 705/2; 705/14.66

(58) Field of Classification Search .................. 705/2–4, 705/14.4, 14.49–14.67, 14.73
See application file for complete search history.

(56) References Cited

U.S. PATENT DOCUMENTS

| | | | | |
|---|---|---|---|---|
| 6,067,524 A * | 5/2000 | Byerly et al. | ..................... | 705/3 |
| 6,240,394 B1 * | 5/2001 | Uecker et al. | ..................... | 705/3 |
| 2002/0016529 A1 * | 2/2002 | Iliff | .............................. | 600/300 |
| 2003/0050799 A1 * | 3/2003 | Jay et al. | ........................... | 705/2 |
| 2004/0172295 A1 * | 9/2004 | Dahlin et al. | ..................... | 705/2 |
| 2005/0209890 A1 * | 9/2005 | Kong | ................. | 705/3 |
| 2008/0208986 A1 * | 8/2008 | Kobylevsky et al. | ......... | 709/206 |
| 2009/0125324 A1 * | 5/2009 | Keravich et al. | ................. | 705/2 |

* cited by examiner

*Primary Examiner* — Gerald J. O'Connor
*Assistant Examiner* — Mark Holcomb
(74) *Attorney, Agent, or Firm* — Francis C. Kowalik; Marshall, Gerstein & Borun LLP; Randall G. Rueth (57) ABSTRACT

A system and method may transmit and display marketing information to a customer based on a diagnosed or a probable disease of the customer. One or more databases may store disease state progression data including one or more disease records each including a disease state and each disease state including a symptom. The database may also store healthcare product data including marketing data and a tag corresponding to the marketing data, the tag including one or more elements describing a relationship between the marketing data and a disease record. Customer data may also be stored including health history data corresponding to one or more symptoms. A tag corresponding to the marketing data may then be matched to each symptom of the customer's health history data and the marketing data corresponding to each matched tag may then be transmitted to the customer's web-enabled computing device.

19 Claims, 5 Drawing Sheets

| Primary HIV infection | Clinical stage 1 | Clinical stage 2 | Clinical stage 3 | Clinical stage 4 |
|---|---|---|---|---|
| 0 | 12 | 36 | 60 | 120 |
| Asymptomatic | Asymptomatic | Moderate and unexplained weight loss (<10% of presumed or measured body weight) | A) Conditions where a presumptive diagnosis can be made on the basis of clinical signs or simple investigations: | A) Conditions where a presumptive diagnosis can be made on the basis of clinical signs or simple investigations: |
| Acute retroviral syndrome | Persistent generalized lymphadenopathy | Recurrent respiratory tract infections (such as sinusitis, bronchitis, otitis media, pharyngitis) | Unexplained chronic diarrhea for longer than one month | HIV wasting syndrome |
| | | Herpes zoster | Unexplained persistent fever (intermittent or constant for longer than one month) | Pneumocystis pneumonia |
| | | Recurrent oral ulcerations | Severe weight loss (>10% of presumed or measured body weight) | Recurrent severe or radiological bacterial pneumonia |
| | | Papular pruritic eruptions | Oral candidiasis | Chronic herpes simplex infection (orolabial, genital or anorectal of more than one month's duration) |
| | | Angular cheilitis | Oral hairy leukoplakia | Oesophageal candidiasis |
| | | Seborrhoeic dermatitis | Pulmonary tuberculosis (TB) diagnosed in last two years | Extrapulmonary Tuberculosis |
| | | Fungal finger nail infections | Severe presumed bacterial infections (e.g. pneumonia, empyema, meningitis, bacteraemia, pyomyositis, bone or joint infection) | Kaposi's sarcoma |
| | | | Acute necrotizing ulcerative stomatitis, gingivitis or periodontitis | Central nervous system toxoplasmosis |
| | | | | HIV encephalopathy |
| | | | B) Conditions where confirmatory diagnostic testing is necessary: | B) Conditions where confirmatory diagnostic testing is necessary: |
| | | | Unexplained anaemia (< 80 g/l), and or neutropenia (<500/µl) and or thrombocytopenia (<50 000/µl) for more than one month | Extrapulmonary cryptococcosis including meningitis |
| | | | | Disseminated non-tuberculous mycobacteria infection |
| | | | | Progressive multifocal leukoencephalopathy |
| | | | | Candida of trachea, bronchi or lungs |
| | | | | Cryptosporidiosis |
| | | | | Isosporiasis |
| | | | | Visceral herpes simplex infection |

SYSTEM AND METHOD FOR DISEASE STATE MARKETING

CROSS-REFERENCE TO RELATED PATENT APPLICATIONS

This application claims priority to U.S. Provisional Application No. 61/264,040, filed Nov. 24, 2009, which is hereby incorporated by reference in its entirety.

TECHNICAL FIELD

The present disclosure generally relates to a system and method for marketing health care products to patients, and, more particularly, to marketing health care products that are known to assist patients that have been diagnosed with a particular condition or disease according to a typical progression of the disease.

BACKGROUND

Patients that have been diagnosed with certain conditions or diseases are often unsure or unaware of how to best manage their health. While the best advice to these patients often comes from their immediate health care professional, these professionals often have limited time to spend with each patient. Typically, once a patient has been diagnosed with a disease, their healthcare provider prescribes a course of treatment based on the patient's present symptoms. The prescribed course of treatment might include prescription and over-the-counter (OTC) medications as well as instructions for using the medications. In addition to the medications, the healthcare provider might prescribe a rehabilitative, therapeutic, or assistive regimen as well as devices or products that are known to alleviate the patient's condition. Periodic, follow-up evaluations of the patient allow the healthcare professional to adjust the course of treatment according to the symptoms exhibited and described by the patient.

Most diseases and other health ailments progress in a known manner. Years of study have allowed healthcare professionals to compile data related to the symptoms and conditions that patients typically exhibit as the patient's disease state progresses. Disease state progression may include one or more stages during which a patient typically exhibits symptoms indicating known conditions related to the disease. Describing a disease state progression by stages is a valuable tool for both healthcare professionals and their patients. For example, if a patient begins to exhibit symptoms indicating a particular condition of one disease stage, the healthcare professional may also test for other conditions that are typically exhibited by other patients who have been similarly diagnosed as a precaution. The disease state progression also gives the patient some level of comfort in knowing what to expect with their disease. This knowledge enables patients to plan for various symptoms that may be associated with the disease over time.

However, most planning and treatment regarding the disease state progression is entirely between the healthcare professional and the patient. As the patient encounters typical symptoms or conditions, he or she consults with their healthcare professional who then determines how best to treat the disease according to known best practices. However, due to the limited amount of time the professional is able to spend with the patient, the patient might not be fully aware of the wide array of beneficial healthcare products that are available to treat various conditions associated with the disease. Further, a patient in an early stage of a disease might not be aware that the disease is entering an advanced stage, yet might be experiencing some minor symptoms that indicate such disease state progression. For example, a patient diagnosed with an HIV infection and exhibiting symptoms associated with Clinical Stage 1 (see FIG. 1D) may experience a recurrent respiratory tract infection that is an indication of Clinical Stage 2. While the patient might not presently exhibit other Clinical Stage 2 conditions, it is likely that the patient will exhibit these conditions as the disease progresses. Yet, given the limited amount of time each healthcare professional is able to spend with each patient, it is impossible for the professional to recommend every product that might alleviate the patient's present and future conditions as the disease progresses. Because of the limited opportunity healthcare professionals and patients have to discuss symptom-relieving OTC products, the patient may also suffer from a lack of complete information.

BRIEF DESCRIPTION OF THE DRAWINGS

FIG. 1D illustrates exemplary disease state progression, in accordance with the described embodiments.

DETAILED DESCRIPTION

Figure 1A:
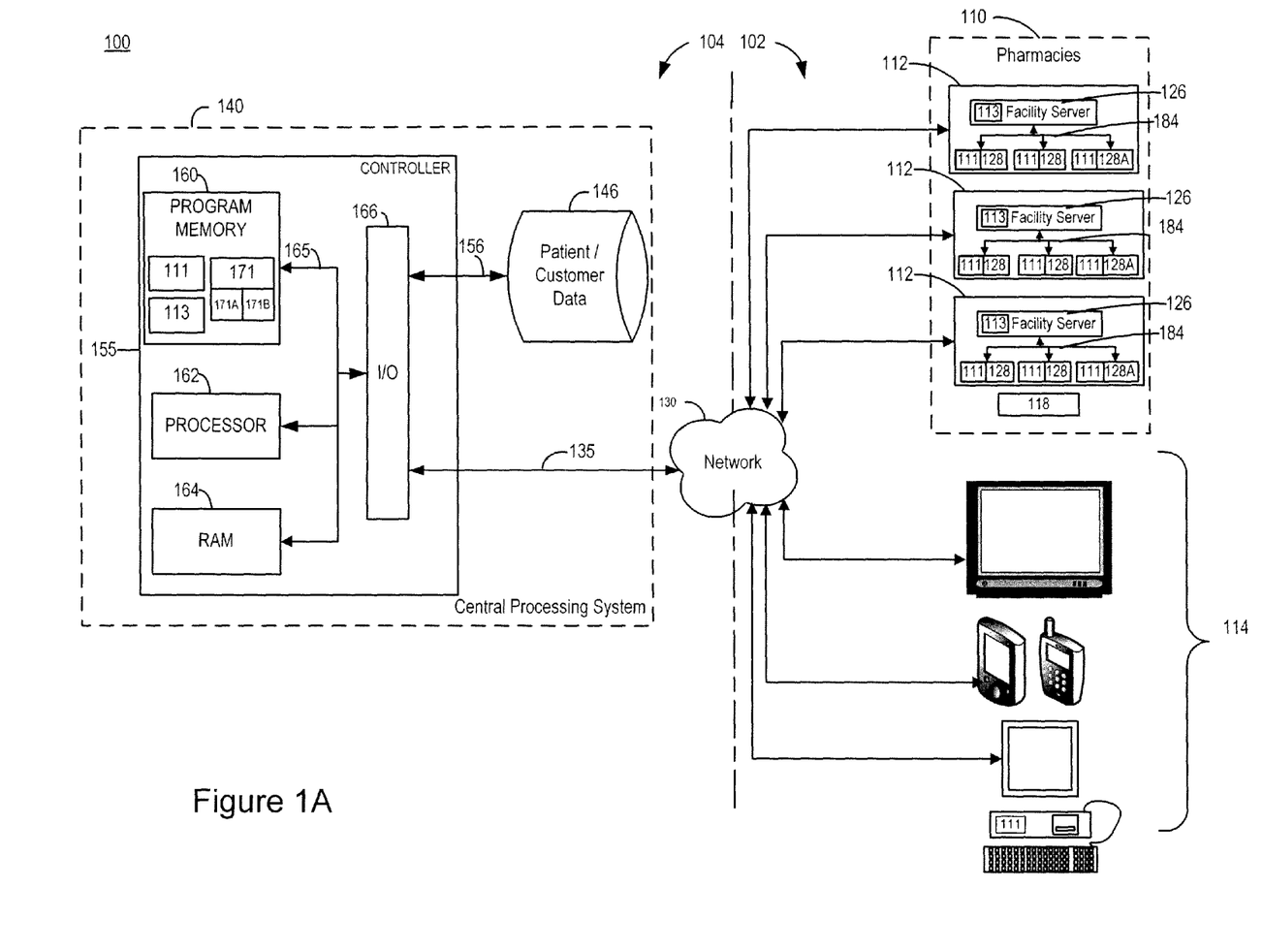
FIG. 1A illustrates a block diagram of a computer network and system on which an exemplary disease state progression marketing system and method may operate in accordance with the described embodiments.
Figure 1B:
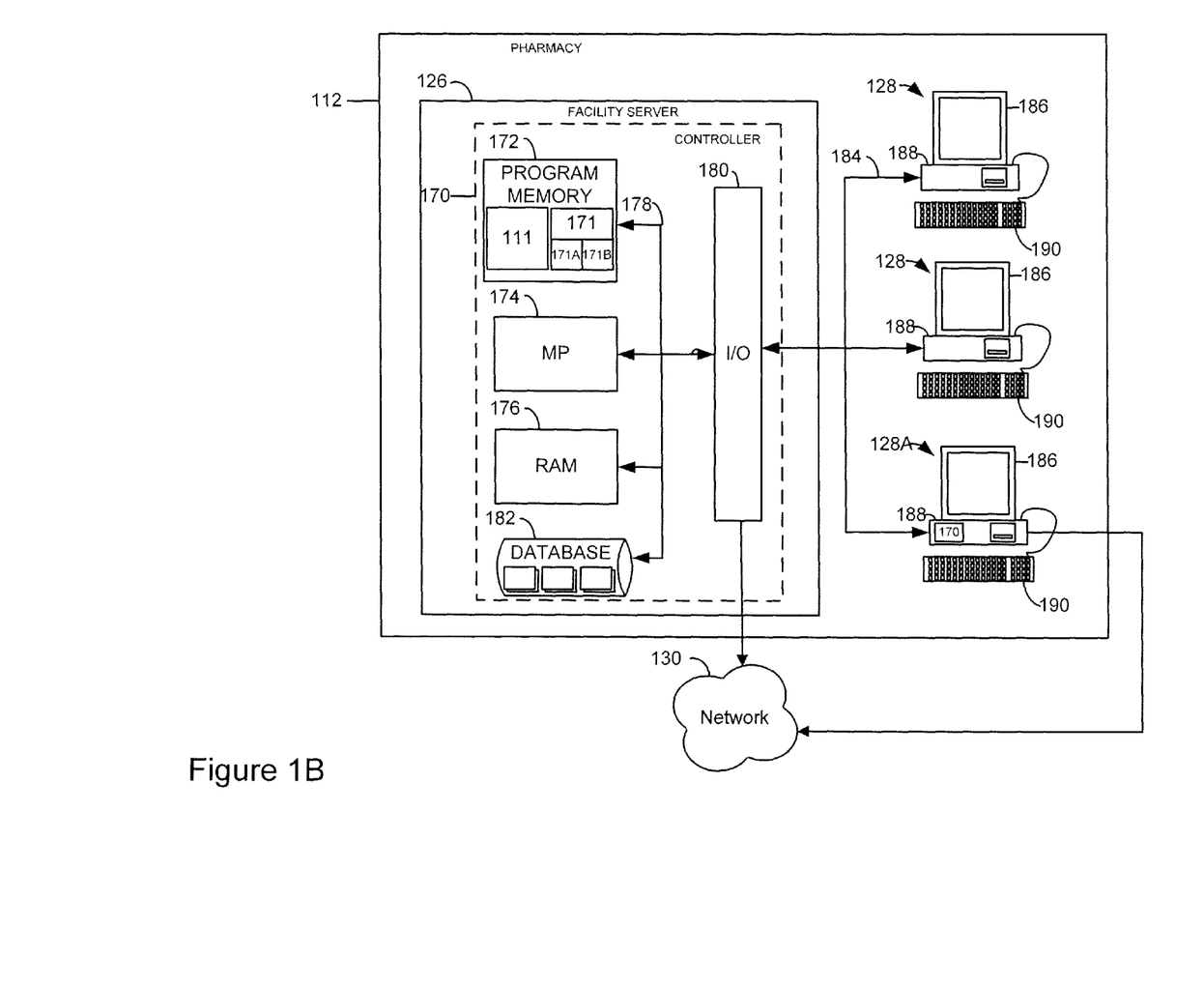
FIG. 1B illustrates a block diagram of a computer server and computer terminals on which an exemplary disease state progression marketing system and method may operate in accordance with the described embodiments.
Figure 1C:
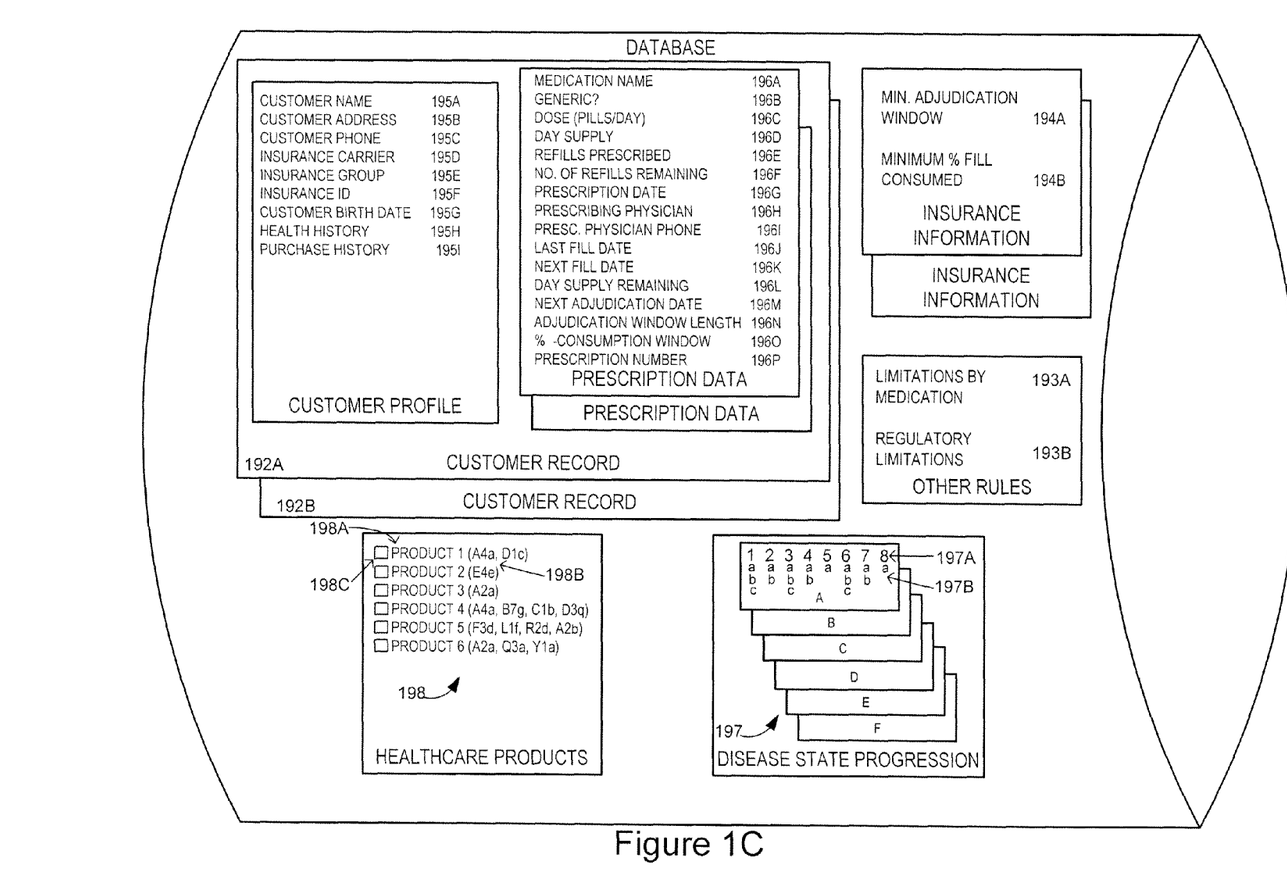
FIG. 1C illustrates exemplary data in a database stored in either of FIG. 1A or FIG. 1B, in accordance with the described embodiments.

FIGS. 1A, 1B, and 1C illustrate various aspects of an exemplary architecture implementing a disease state progression marketing system 100. In particular, FIG. 1A illustrates a block diagram of the exemplary disease state progression marketing system 100. The high-level architecture includes both hardware and software applications, as well as various data communications channels for communicating data between the various hardware and software components. The disease state progression marketing system 100 may be roughly divided into front-end components 102 and back-end components 104. The front-end components 102 are primarily disposed within a retail network 110 including one or more pharmacies 112. The pharmacies 112 may be located, by way of example rather than limitation, in separate geographic locations from each other, including different areas of the same city, different cities, or even different states. The front-end components 102 comprise a number of pharmacy workstations 128. The pharmacy workstations 128 are local computers located in the various pharmacies 112 throughout the retail network 110 and executing various pharmacy management-related applications. Pharmacists, technicians, and other pharmacy personnel, referred to collectively herein simply as "pharmacists" (not shown), use the pharmacy workstations 128 to access customer information, enter new prescriptions, access insurance and payment information and so forth. Each of the pharmacies 112 may be, for example, an in-store retail pharmacy, an on-line pharmacy, a mail-order pharmacy, a long-term care pharmacy, a workplace/on-site pharmacy, or a specialty pharmacy. Retail network 110 may also include one or more warehouses or central-filling facilities 118. The warehouses or central-filling facilities 118 may distribute medications to the various retail pharmacies 112 in the retail network 110, or may distribute medications directly to customers. Web-enabled devices 114 (e.g., personal computers, cellular phones, smart phones, web-enabled televisions, etc.) may be communicatively connected to pharmacies 112 and the system 140 through a digital network 130, as described below.

As used herein, the term "prescription medication" may be read to mean any substance that may be distributed by a pharmacy or by a pharmacist to a patient with the authorization of state-registered, qualified medical doctor. The term "medication" may be read to mean any substance that may be distributed without a prescription to a patient or customer by a pharmacy or by a pharmacist (i.e., OTC substances such as vitamins, nutriceuticals, and supplements). The term "health product" may be read to mean any device that may be distributed without a prescription to a patient that alleviates a physical ailment or disease symptom (i.e., a humidifier, a cane, a wheelchair, a heating pad, etc.).

Returning now to FIG. 1A, those of ordinary skill in the art will recognize that the front-end components 102 could also comprise a plurality of facility servers 126 and web-enabled devices 114 disposed at the plurality of pharmacies 112 instead of, or in addition to, a plurality of pharmacy workstations 128. Each of the pharmacies 112 may include one or more facility servers 126 that may facilitate communications between the web-enabled devices 114 and the back-end components 104 via a digital network 130, described below, and between the terminals 128, 128A of the pharmacies 112 via the digital network 129, and may store information for a plurality of customers/employees/accounts/etc. associated with each facility. Of course, a local digital network 184 may also operatively connect each of the workstations 128 to the facility server 126. Unless otherwise indicated, any discussion of the workstations 128 also refers to the facility servers 126 and the web-enabled devices 114, and vice versa. Moreover, environments other than the pharmacies 112, such as the kiosks, call centers, and Internet interface terminals may employ the workstations 128, the web-enabled devices 114, and the servers 126. As used herein, the term "pharmacy" refers to any of these points of contact (e.g., call centers, kiosks, Internet interface terminals, etc.) in addition to the retail pharmacies 112, etc. described above.

The front-end components 102 communicate with the back-end components 104 via the digital network 130. One or more of the front-end components 102 may be excluded from communication with the back-end components 104 by configuration or by limiting access due to security concerns. For example, the web enabled devices 114 may be excluded from direct access to the back-end components 104. In some embodiments, the pharmacies 112 may communicate with the back-end components via the digital network 130. In other embodiments, the pharmacies 112 and web-enabled devices 114 may communicate with the back-end components 104 via the same digital network 130, but digital access rights, IP masking, and other network configurations may deny access of the web-enabled devices 114.

The digital network 130 may be a proprietary network, a secure public Internet, a virtual private network or some other type of network, such as dedicated access lines, plain ordinary telephone lines, satellite links, combinations of these, etc. Where the digital network 130 comprises the Internet, data communication may take place over the digital network 130 via an Internet communication protocol. The back-end components 104 include a central processing system 140 within a central processing facility, such as, for example, the central processing facility described in U.S. patent application Ser. No. 12/271,686 entitled "DISTRIBUTED PHARMACY PRESCRIPTION PROCESSING SYSTEM" the entire disclosure of which is incorporated by reference herein. Of course, the pharmacies 112 may be communicatively connected to different back-end components having one or more functions or capabilities that are similar to the central processing system 140 (e.g., a processing system 141, 142). The central processing system 140 may include one or more computer processors 162 adapted and configured to execute various software applications and components of the disease state progression marketing system 100, in addition to other software applications, such as a medication management system. The central processing system 140 further includes a database 146. The database 146 is adapted to store data related to the operation of the disease state progression marketing system 100 (e.g., patient profile data including diagnoses, past healthcare product and medication purchases, prescription histories, etc.) The central processing system 140 may access data stored in the database 146 when executing various functions and tasks associated with the operation of the disease state progression marketing system 100.

Although the disease state progression marketing system 100 is shown to include a central processing system 140 in communication with three pharmacies 112, and various web-enabled devices 114 it should be understood that different numbers of processing systems, pharmacies, and devices may be utilized. For example, the digital network 130 (or other digital networks, not shown) may interconnect the system 100 to a plurality of included central processing systems 140, hundreds of pharmacies 112, and thousands of web-enabled devices 114. According to the disclosed example, this configuration may provide several advantages, such as, for example, enabling near real-time uploads and downloads of information as well as periodic uploads and downloads of information. This provides for a primary backup of all the information generated in the process of updating and accumulating pharmacy and patient/customer data and marketing health products to customers based on disease state progression. Alternatively, some of the pharmacies 112 may store data locally on the facility server 126 and/or the workstations 128.

FIG. 1A also depicts one possible embodiment of the central processing system 140. The central processing system 140 may have a controller 155 operatively connected to the database 146 via a link 156 connected to an input/output (I/O) circuit 166. It should be noted that, while not shown, additional databases may be linked to the controller 155 in a known manner.

The controller 155 includes a program memory 160, the processor 162 (may be called a microcontroller or a microprocessor), a random-access memory (RAM) 164, and the input/output (I/O) circuit 166, all of which are interconnected via an address/data bus 165. It should be appreciated that although only one microprocessor 162 is shown, the controller 155 may include multiple microprocessors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM(s) 164 and the program memories 160 may be implemented as semiconductor memories, magnetically readable memories, and/or optically readable memories, for example. A link 135 may operatively connect the controller 155 to the digital network 130 through the I/O circuit 166.

FIG. 1B depicts one possible embodiment of the front-end components 102 located in one or more of the pharmacies 112 from FIG. 1A. Although the following description addresses the design of the pharmacies 112, it should be understood that the design of one or more of the pharmacies 112 may be different than the design of others of the pharmacies 112. Also, each of the pharmacies 112 may have various different structures and methods of operation. It should also be understood that while the embodiment shown in FIG. 1B illustrates some of the components and data connections that may be present in a pharmacy 112, it does not illustrate all of the data connections that may be present in a pharmacy 112. For exemplary purposes, one design of a pharmacy is described below, but it should be understood that numerous other designs may be utilized.

Each of the pharmacies 112 has one or more pharmacy workstations 128 and/or a facility server 126. The digital network 184 operatively connects the facility server 126 to the plurality of workstations 128 and/or to the web-enabled devices 114. The digital network 184 may be a wide area network (WAN), a local area network (LAN), or any other type of digital network readily known to those persons skilled in the art. The digital network 130 may operatively connect the facility server 126, the workstations 128, and/or the web-enabled devices 114 to the central processing system 140.

Each workstation 128, client device terminal 128A, or facility server 126 includes a controller 170. Similar to the controller 155 from FIG. 1A, the controller 170 includes a program memory 172, a microcontroller or a microprocessor (MP) 174, a random-access memory (RAM) 176, and an input/output (I/O) circuit 180, all of which are interconnected via an address/data bus 178. In some embodiments, the controller 170 may also include, or otherwise be communicatively connected to, a database 182. The database 182 (and/or the database 146 of FIG. 1A) includes data such as customer records 192, insurer information records 194, and other rules 199 and miscellaneous information 193 (as depicted in FIG. 1C). As discussed with reference to the controller 155, it should be appreciated that although FIG. 1B depicts only one microprocessor 174, the controller 170 may include multiple microprocessors 174. Similarly, the memory of the controller 170 may include multiple RAMs 176 and multiple program memories 172. Although the figure depicts the I/O circuit 180 as a single block, the I/O circuit 180 may include a number of different types of I/O circuits. The controller 170 may implement the RAM(s) 176 and the program memories 172 as semiconductor memories, magnetically readable memories, and/or optically readable memories, for example.

Either or both of the program memories 160 (FIG. 1A) and 172 may also contain a disease state progression marketing engine 171, for execution within the processors 162 (FIG. 1A) and 174, respectively. The disease state progression marketing engine 171 may perform the various tasks associated with the disease state progression marketing method (FIG. 2, described below), and may be a single module 171 or a plurality of modules 171A, 171B. While the engine 171 is depicted in FIGS. 1A and 1B as including two modules, 171A and 171B, the engine 171 may include any number of modules to effectively market medications and health products to customers based on a disease state progression, as described herein. By way of example and not limitation, the disease state progression marketing engine 171 or the modules 171A and 171B within the disease state progression marketing engine 171 may: receive disease information from a web-enabled device; access and retrieve disease state progression data; access and retrieve patient data including prescription medication, medication, health product purchase information, and other patient information; determine a likely disease state for the patient based on one or more of the disease state progression, prescription medication, OTC medication, health product purchase information, and other patient data; access and retrieve information for medications and health products that are identified as alleviating conditions and symptoms of the patient's actual or likely disease state; provide the information to the patient; etc. The disease state progression marketing engine 171 and/or each of the modules 171A, 171B may execute one or more of the various portions of the disease state progression marketing method 200 described below with reference to FIG. 2.

In addition to the controller 170, the workstations 128 and the web-enabled devices 114 may further include a display 186 and a keyboard 190 as well as a variety of other input/output devices (not shown) such as a scanner, printer, mouse, touch screen, track pad, track ball, isopoint, voice recognition system, digital camera, etc. A pharmacy employee may sign on and occupy each workstation 128 or client device terminal 128A to assist the pharmacy employee in performing his or her duties. Pharmacy employees may sign onto the workstation 128 or the client device terminal 128A using any available technique, such as entering a user name and password. If a pharmacy employee signs on to the system using a client device terminal 128A, the network 184 communicates this information to the facility server 126, so that the controller 170 may identify which pharmacy employees are signed onto the system 100 and which workstation 128 or client device terminal 128A the employee is signed onto. This may be useful for record keeping and/or monitoring the pharmacy employees' productivity as well as in record-keeping or routing prescription transfers to pharmacists who are authorized to accept controlled prescriptions, or other transfer tasks requiring various levels of authority or access corresponding to a login identification or other information.

Various software applications resident in the front-end components 102 and the back-end components 104 implement the disease state progression marketing methods, and provide various user interface means to allow users (i.e., pharmacists and/or customers) to access the system 100. One or more of the front-end components 102 and/or the back-end components 104 may include a user-interface application 111 for allowing a user, such as the patient, the pharmacist, or a customer service representative, to input and view data associated with the system 100, and to initiate disease state progression marketing. In one embodiment, the user interface application 111 is a web browser client, and the facility server 126 or the central processing system 140 implements a server application 113 for providing data to the user interface application 111. However, the user interface application 111 may be any type of interface, including a proprietary interface, and may communicate with the facility server 126 or the central processing system 140 using any type of protocol including, but not limited to, file transfer protocol (FTP), telnet, hypertext-transfer protocol (HTTP), etc. Moreover, some embodiments may include the user interface application 111 running on one of the web-enabled devices 114 (as when a patient is accessing the system), while other embodiments may include the application 111 running on one of the workstations 128 in a pharmacy 112. The information sent to the workstations 128 and to the web-enabled devices 114 from the facility server 126 and/or the central processing system 140 includes data retrieved from the database 146 and/or the database 182. The central processing system 140 and/or the facility server 126 may implement any known protocol compatible with the user-interface application 111 running on the workstations 128 and the web-enabled devices 114 and adapted to the purpose of receiving and providing the necessary patient/customer and disease state information for marketing the most beneficial medications and health products to the patients, according to their actual disease state or a predicted disease state, as further described below.

For purposes of implementing the disease state progression marketing system 100, the primary point of contact for the customer is the pharmacy 112, central processing system 140 through the user interface application 111, or a call center representative. Typically, a patient or customer may launch or instantiate the user interface application 111 (web browser or other client application) from the user's web enabled device 114 to access a system 140 or server 126 including the disease state progression marketing engine 171 and/or one or more of the modules 171A, 171B through the network 130. As used herein, the term "customer" may be, by way of example, a patient (i.e., the person named on the prescription), a guardian (e.g., the parent of a child named on the prescription), a care-giver (i.e., anyone who takes care of a patient or picks up the medication on the patient's behalf), etc. Moreover, the term "customer" is not limited to a single person, but may instead be any person or persons having a reason or desire to gain information related to medication and other health care products that are known to alleviate certain conditions or symptoms related to a disease state. For example, a customer could be a care-giver responsible for patients with a specific disease that progresses in a known manner. The caregiver customer might greatly benefit from gaining information related to various medications and health products to assist in his or her caregiver responsibilities. In any event, while the term "customer" is used interchangeably with the term "patient," in this specification the term "customer" is used primarily so as to avoid confusion. Thus, a customer may be a patient (as where a person, alone, manages the various states of their disease progression), and a customer may also be, by way of example, a caregiver managing the health of several patients that have been diagnosed with the same disease.

Also, as mentioned above, the pharmacy 112 may be any of the channels through which the entity implementing the disease state progression marketing system 100 serves its pharmacy customers. Thus, the pharmacy 112 may be a retail pharmacy 112 in the customer's neighborhood (or any other drug store in a drug store chain), an on-line pharmacy or an on-line interface to a pharmacy 112 or to a retail network 110 (where the customer uses a web-browser to communicate with the disease state progression marketing engine 171 and/or each of the modules 171A, 171B), a phone/touch-tone interface to a pharmacy 112 or to a retail network 110 (where the customer uses a phone service to communicate with the server application 113), a mail-order pharmacy, a central-filling facility, a specialty pharmacy, or any other type of pharmacy affiliated with the entity implementing the disease state progression marketing system 100.

In some embodiments, a pharmacist, other pharmacy staff, or a customer service representative (all referred to herein simply as "the pharmacist") invokes the disease state progression marketing system 100 while interacting with a customer at a pharmacy 112 or over the telephone (e.g., from a retail pharmacy 112, or a call center). The pharmacist will have access to one of the pharmacy workstations 128 or to one of the web-enabled devices 114 and may invoke the disease state progression marketing system 100. In other embodiments, the customer invokes the disease state progression marketing system 100 (e.g., at a kiosk, via an Internet interface terminal at the pharmacy, in-person, etc.) by requesting disease state progression product information while physically present in a pharmacy 112. In still other embodiments, the customer facilitates or requests the delivery of disease state progression product information remotely (e.g., at kiosk located at the pharmacy 112, a remote Internet interface through a web-enabled device 114, via telephone, etc.). Alternatively, the disease state progression marketing system 100 may be invoked automatically depending on customer preferences or settings. For example, if a customer discloses a particular disease diagnosis during or subsequent to enrollment, the system 100 may be configured by customer settings or automatic default settings to build disease state progression marketing information and deliver such information to the patient. In some embodiments, the customer must deliver consent to the system (e.g., by selecting "I Agree" in an automated consent form displayed to the customer) to begin disease state progression marketing.

As described above, one or both of the databases 146 and 182, illustrated in FIGS. 1A and 1B, respectively, include various information about the pharmacy's customers and the prescriptions filled by the pharmacy, as well as various business information including, but not limited to, information associated with third-party payors (e.g., insurance companies), employee information, and the like. FIG. 1C depicts some of the exemplary data that the system 100 may store on the databases 146 and 182. The databases 146 and/or 182 contain a customer record 192 for every customer who registers his or her information with the disease state progression marketing system 100 via a web site using the user interface application 111, a call center, at one of the pharmacies 112, etc. The customer record 192 contains important information about the customer and the various pharmacy services that have been invoked by, or on behalf of, the customer in a customer profile 195. The customer profile 195 includes basic biographical information about the customer, such as a customer name 195A, a customer address 195B, a customer phone number 195C, an insurance carrier 195D associated with the customer, an insurance group number 195E for the customer, an insurance ID number 195F for the customer, a customer birth date 195G, a health history or condition 195H, customer purchase history, etc.

The health history 195H may include data related to conditions or diseases that the customer has exhibited in the past, or currently exhibits. Typically, the health history 195H is data that is voluntarily inputted by a customer using the user interface application 111. In some embodiments, the customer's health history 195H may be voluntarily provided by the customer or received directly from the customer's healthcare provider upon authorization by the customer. For example, the health history 195H may be communicatively linked to a healthcare provider's patient data system and may periodically receive updates from the provider's system. Alternatively or additionally, the health history 195H may be updated automatically any time the healthcare provider changes the diagnosis of the customer. The health history may also be inferred by using prescription history information. The health history data 195H may include a current customer diagnosis, a date of the diagnosis, a date the customer first exhibited a condition or symptom, a date of injury, a date of an operation, a state of a diagnosed disease that the customer currently exhibits, a probable state of the diagnosed disease that the customer currently exhibits, etc. The health history data may also include data corresponding to a disease 197, a disease state 197A, and a symptom 197B as further explained, below.

The purchase history 195I may include data related to purchases the customer routinely makes or has made at pharmacies 110. For example, a customer may make purchases of several healthcare products such as OTC cold and flu symptom relievers, or may purchase or rent rehabilitative products such as crutches, a cane, a heating pad, bandages, etc. The purchase history data may include any product sold by the pharmacies 110 and purchased by a customer, whether in person or online. Where purchases are made by the customer in the store, the purchase data made be linked to the customer record 192 though credit card, an in-store savings card, or other type of point-of-sale identification. Where the purchases are made by the customer over a network 130 or on-line, the purchases may be linked to the customer record 192 through a web-based profile that is accessible by the customer through a web-enabled device 114, as herein described. The purchase history 195I may also be used by the disease state progression marketing system 100 to interpolate or supplement the health history data 195H.

Additionally, the customer profile 195 may include other information such as credit card information or other payment information, one or more customer e-mail addresses, user name and/or password information, online security question/answer information, etc. Of course, the customer record 192 may also include other, more or less information than that described above or shown in FIG. 1C.

The customer record 192 also includes prescription data 196 for each prescription filled by the pharmacy for the customer. The prescription data 196 generally include, but are not limited to: a name 196A of the medication; an indication 196B whether a generic may be substituted; a dose (i.e., pills per day) 196C of the medication; a number of days of medication to be dispensed (also referred to herein as a "day supply" or a "prescribed day supply") 196D; a number of refills prescribed 196E; a number of refills remaining 196F; a prescription date 196G; a prescribing physician 196H; a phone number 196I for the prescribing physician; a date on which the prescription was most recently adjudicated 196J; a calculated date on which the prescription may next be adjudicated 196K for the prescription; a remaining day supply 196L for the prescription; a percent-consumption period 196O indicating the number of days it would take to consume the required minimum percent-fill consumed 194B of the fill for the prescription); and a prescription number 196P. Of course, the prescription data 196 need not include all of the information above, such as when the system 100 determines some information (e.g., the next adjudication date 196K) but does not store it, or stores it some place other than with the prescription data 196 in the database 146 or the database 182. Moreover, the prescription data 196 may include additional information not mentioned above.

The database 182 and/or the database 146 may also include rules related to disease state progression marketing. In particular, records 193 may include various rules regarding medication or product limitations 193A, and regulatory limitations 193B (e.g., regulations related to specific drugs) that may place limitations on the customers use of a medication or product such as when and how often a customer refills a prescription, how much of a medication or product the customer may receive over a given time period, etc.

The database 182 and/or the database 146 may also include disease stage progression data 197 including data particularly describing the progression of a plurality of customer health conditions including diseases, conditions, post-operation rehabilitation schedules, fitness and weight loss regimens, common sicknesses, and other conditions as may be generally described by the health history data 195H. FIG. 1D illustrates one example of a disease state progression 197 including one or more states 197A of a disease or other condition, each state including one or more conditions or symptoms 197B. The conditions or symptoms 197B may include various categories including, for example, conditions where a presumptive diagnosis can be made on the basis of clinical signs, simple investigations, or even a customer's pharmaceutical and other healthcare product purchase history 195I, conditions where confirmatory diagnostic testing is necessary, etc. The progressions 197 may be input into the databases 182, 146 using several methods including manual input by a pharmacy employee, automatic input from inferred disease state progression derived from prescription history, automatic input via communication with a government agency or a private organization that investigates and formulates the progression of disease states, etc. Some examples of such agencies include the World Health Organization (WHO), the Center for Disease Control (CDC), the Agency for Toxic Substances and Disease Registry (ATSDR), the National Institutes for Health (NIH), etc. Further, regarding a progression 197 that reflects a customer's post-operation recovery schedule or other rehabilitative schedule, this type of progression may be particularly tailored for the customer and received directly from a healthcare provider. For example, a progression 197 for a rehabilitation schedule or other personalized progression may include one or more states 197A of recovery, each state including one or more conditions that the customer will likely exhibit during that recovery state. In some embodiments, a healthcare professional that prescribes the recovery schedule, rehabilitation schedule, or other personalized schedule, may automatically or manually send the schedule to the disease state progression marketing system 100 via any of the methods described herein. In some embodiments, the progression data 197 may also include time period data 197C. For example, the time period data 197C may indicate a projected time after diagnosis that typical patients exhibit a particular stage 197A and condition 197B. As described above, the health history data 195H may include a date of diagnosis, a date the customer first exhibited a symptom or condition of a disease, a date of injury, a date of an operation, etc. When the disease state progression 197 includes a diagnosed disease, the time period data 197C may indicate a projected time after diagnosis that typical patients exhibit a particular stage 197A and condition 197B. When the disease state progression 197 includes a rehabilitation plan, post-operative recovery plan, or other personalized progression, the time period data 197C may indicate how long a typical customer receiving such an injury or undergoing such an operation may be expected to exhibit conditions 197B after a date of injury or operation (e.g., two weeks after removing a cast following the customer's leg injury or operation, the customer should exhibit minor calf stiffness and should perform twenty calf raises, etc.). In further embodiments, the time period data 197C may be dynamic such that the time period data 197C may change based on the health history data 195H described above. For example, a particular customer may exhibit an abnormal disease state progression that does not conform exactly to the typical progression of the disease corresponding to the disease state progression 197C (e.g., a customer may be diagnosed with symptoms of Clinical Stage Two at twenty-eight months since the customer was initially diagnosed, rather than a typical thirty-six months). Where the customer exhibits an abnormal disease state progression, the time period data 197C may be increased or decreased to reflect a more accurate state of the customer's actual disease state progression.

With reference to FIG. 1C, the databases 182, 146 may include a plurality of disease state progressions 197, each progression including one or more states 197A, (e.g., 1-8, etc.), wherein each state includes one or more conditions or symptoms (e.g., a, b, c, etc.) 197B. While FIG. 1C depicts six disease state progressions 197 including eight states of progression and three possible conditions or symptoms, the database 182, 146 may include any number of progressions 197 each including any number of states 197A that includes any number of conditions or symptoms 197B. As described above, the progressions 107 may correspond to any diseases, recovery and rehabilitation schedules, common ailments with known progression states, etc.

With further reference to FIG. 1C, the databases 182, 146 may also include data corresponding to a plurality of healthcare products 198. The healthcare products may be any commercial product that may be used in the treatment or diagnosis of a customer's physical condition or symptom. For example, the healthcare products may include prescription and OTC medications, healthcare supplies such as cotton balls, elastic bandages, oxygen canisters, leg braces, walkers and canes, crutches, herbal or alternative medicaments, etc. Each healthcare product data 198A may also include a tag 198B corresponding to data within one or more disease state progressions 197. The tag 198B may include data corresponding to one or more progressions 197, disease states 197A, and one or more conditions or symptoms 198B. In some embodiments, the tag 198B is a tuple including one or more elements describing a relationship between a healthcare product 198A and an element within a disease state progression 197. For example, a Product 1 may be tagged as alleviating or treating one or more of a particular disease (e.g., disease 'A'), disease state (e.g., state '4' of disease 'A'), and disease condition or symptom (e.g., condition 'a' of state '4' and disease 'A'). Of course, many other elements may be used within the tag 198B to identify a particular healthcare product 198A as helpful to treat a customer ailment or other physical condition. For example, a tag 198B may include a classification identifier that identifies the product as treating a class of diseases or ailments (e.g., aspirin is known to treat a wide variety of conditions. Rather than including an individual tuple for each possible condition that is able to be treated by aspirin, such healthcare products may include a tag 198B that associates the product with a class of conditions such as "pain" or "inflammation").

Generating and sending disease state progression information from the central processing system 140 to the customer may include inputting various data about the customer and his or her current condition using the disease state progression marketing system 100 and, in particular, into the disease state progression marketing engine 171. In some embodiments, the customer inputs the various data using the disease state progression marketing engine 171 and modules 171A, 171B by logging into the disease state progression marketing system 100 through the Internet interface terminal 126 or web-enabled device 114 (e.g., through a personal computer, smart phone, or other device connected to the Internet) or through an access terminal or kiosk 122. In another embodiment, a pharmacist or customer service representative accesses the disease state progression marketing system 100. In any event, the user-interface software 111 running on the web-enabled device 114 receives a series of web pages (or other data) from the server application 113. The web pages may provide the customer with information and instructions, and allow the customer to input disease and disease state information into the disease state progression marketing engine 171 and modules 171A, 171B and permit selections related to the marketing of medications and products to the customer according to his or her actual or predicted disease state.

In an alternate embodiment, a customer service representative (e.g., at a call-center) or pharmacy employee inputs the various data into the disease state progression marketing engine 171 by logging into the system 100 through the workstation 128 at a call-center or personal computer. The user-interface software 111 running on the workstation 128 receives a series of web pages (or other data) from the server application 113. The web pages provide the customer service representative or customer with information and instructions, and allow the customer service representative or customer to input information into the disease state progression marketing engine 171 and make selections related to the marketing of medications and products to the customer according to his or her actual or predicted disease state. The information entered by the customer or the customer service representative may then be forwarded to the disease state progression marketing engine 171 in general, and the databases 146, 182 in particular to be used in the marketing of medications and products to the customer according to his or her actual or predicted disease state, as further described below.

While one embodiment, described herein, uses web pages to convey and receive information, any reference to a "web page" or a "page" could also refer to a screen presented by any proprietary or non-proprietary user-interface application 111. This may include any way of displaying information, including the use of a pop-up window, a modal-window, an overlay screen, etc. As generally known in the art, the display elements may include text (some of which text may serve as links to additional information or other screens or web pages), data entry boxes or text fields, pull-down lists, radio buttons, check boxes, images, and buttons. Throughout this specification, it is assumed that the customer activates the various elements (e.g., buttons, pull-down lists, links, etc.) of the screen or web page using a mouse or other pointing device. Thus, throughout the specification, the terms "click" and "clicking" may be used interchangeably with the terms "select," "activate," or "submit" to indicate the selection or activation of one of the elements. Of course, other methods (e.g., keystrokes, voice commands, etc.) may also be used to select or activate the various elements. Moreover, throughout this specification, the terms "link" and "button" are used interchangeably to refer to a graphic representation of a command that may be activated by clicking on the command.

Regardless of the precise embodiments of the user-interface application 111 and the server application 113, the user-interface application 111 communicates information to and from the server application 113. For example, the server application 113 provides customer, prescription, and disease state marketing information to the user-interface application 111. The user-interface application 111 formats and/or displays the received information, accepts input from a user (e.g., a pharmacist, customer, or customer service representative) and transmits the input back to the server application 113. Throughout this specification, it should be understood that some portion of the data displayed by the user-interface application 111 originates at the server application 113, and that the user-interface application 111 transmits data entered by the user back to the server application 113 to the various components and modules of the disease state progression marketing system 100, including the disease state progression marketing engine 171 and various databases 146, 182.

Figure 2:
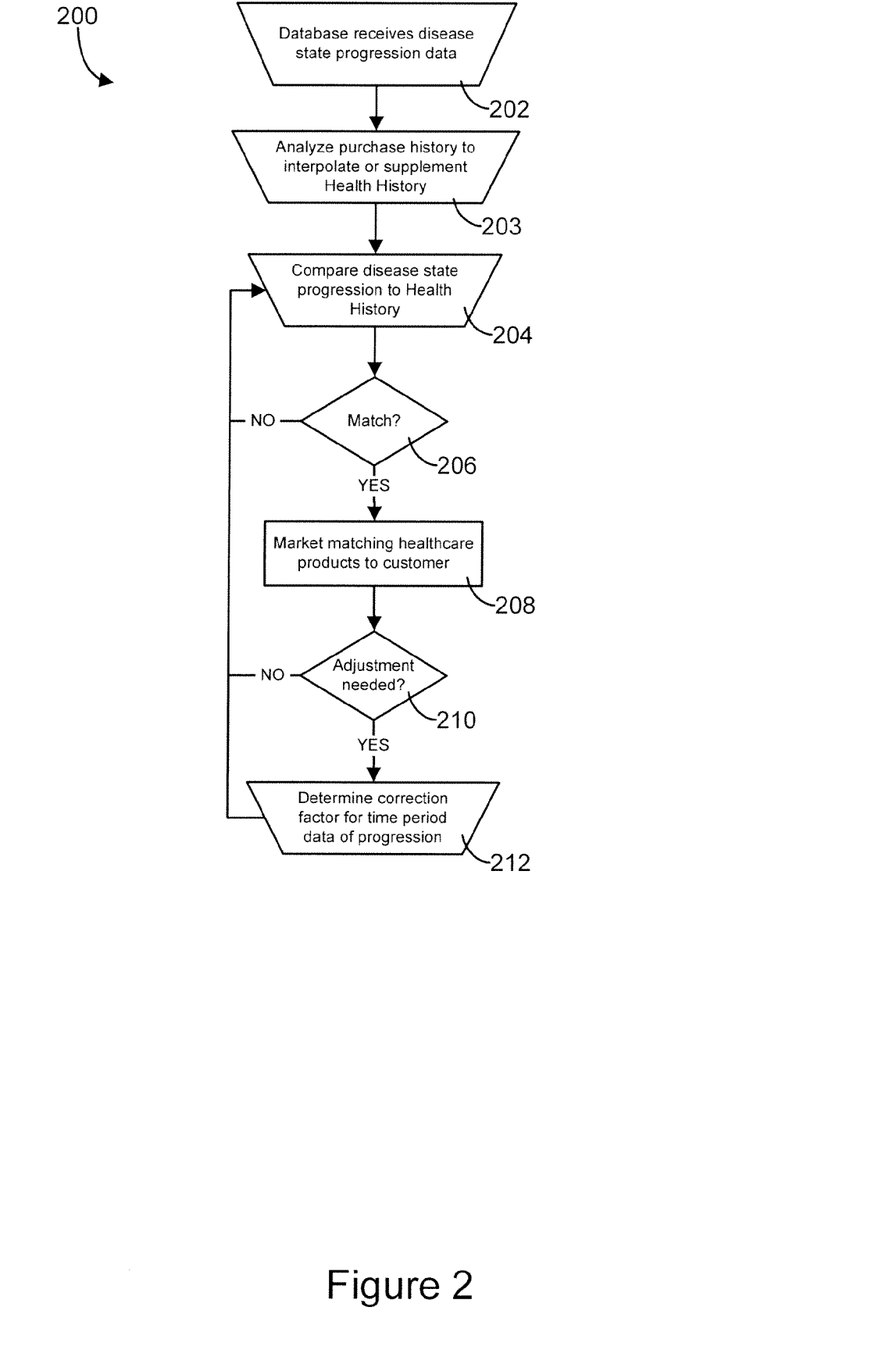
FIG. 2 illustrates an exemplary block diagram of a flow chart for one embodiment of a method for disease state progression marketing.

A method 200 (FIG. 2) for marketing particular healthcare products to a customer according to a disease state progression associated with the customer may include one or more functions that may be stored as computer-readable instructions on a computer-readable storage medium, such as a program memory 160, 172, including the user-interface application 111, disease state progression marketing engine 171, and various modules (e.g., 171A, 171B), as described above. The instructions are generally described below as "blocks" or "function blocks" proceeding as illustrated in the flowchart of FIG. 2. While the blocks of FIG. 2 are numerically ordered and described below as proceeding or executing in order, the blocks may be executed in any order that would result in the transferal of a prescription from one pharmacy to another, as described herein.

FIG. 2 illustrates one embodiment of a method 200 for marketing particular healthcare products to a customer according to a disease state progression associated with the customer. Of course, due to the sensitive nature of customer's health information, including privacy interests and various law and regulations, the use of disease state marketing may be purely voluntary for the customer and in complete compliance with all privacy laws and regulations regarding customer data. In some embodiments, the database 182, 146 may receive disease state progression data 197 including one or more stages 197A, wherein each stage includes one or more conditions or symptoms 197B. The data 197 may be received via any known data transmission techniques including electronic data transmission techniques that employ TCP/IP, and other methods. As described above, the disease state progression data may be automatically or manually entered into the database 182, 146 and received from a third party such as the customer's healthcare provider or an official organization such as CDC, WHO, NIH, or any other entity that is able to provide disease state progression data 197, or directly from the customer. Alternatively or additionally, the database 182, 146 may receive disease state progression data 197 in the form of a rehabilitation plan, a treatment plan, a fitness or weight loss regimen, or other type of information from the customer himself, the customer's healthcare provider, or another entity. When the data 197 includes a rehabilitation or other plan, the data 197 may include rehabilitation or treatment stages 197A that each include conditions 197B that the customer likely exhibits during the stage. As described above, the data 197 may be personalized according to particular conditions or symptoms that the customer exhibits by, for example, dynamically changing time period data 197C, as described herein.

At block 203, the method 200 may analyze the purchase history information 195I to interpolate information to substitute for or supplement a customer's health history data 195H. In some embodiments, the method 200 may gather information related to customer purchases related to health care products 198 to predict a disease state of the customer. For example, the customer may purchase one or more products that have been identified as helpful in the treatment of herpes zoster and angular cheilitis. Each product, as previously described in relation to FIG. 10, may include a tag 198B (e.g., a tuple) that corresponds to information that may be used to tie any particular product or combination of products to the treatment of one or more conditions 197B during a clinical stage 197A of a disease or other regimen 197. Continuing with the previous example, the products the customer purchased to treat herpes zoster and angular cheilitis may each include a tag 198 of "A2a" (e.g., Product 3 and Product 6) indicating that the products are generally used to treat Disease "A," Clinical Stage "2," and Condition "a." As the customer makes more purchases of products that indicate a pattern of the same disease and clinical stage, the method 200 may interpolate that the customer is suffering from a particular disease in a particular stage without having any further health history information. Of course, some products may be only useful for very specific diseases and stages, thus, more or less customer purchase information may be needed for the method 200 to interpolate a disease and stage for the customer. Further, the purchase information 195I may be combined with customer health history data 195H to formulate an increasingly accurate picture of the customer's health.

In other embodiments, the system 100 and method 200 may use prescription information from different physicians to interpolate a disease state or condition for which the customer has not yet been diagnosed. Further, prescription or OTC product purchase information could be sent to the different prescribing physicians. Using this information, the different physicians may determine if a combination of prescriptions that are normally used to treat specific symptoms or conditions indicates that the customer is suffering from a disease that no single physician or the customer had previously ascertained. For example, physician "A" may prescribe a first medication to treat a customer's cheilitis while physician "B" may prescribe a second medication to treat herpes zoster for the same customer. The combination of cheilitis and herpes zoster may indicate clinical stage 2 of an HIV infection. However, the customer may not have been previously diagnosed with HIV and both physicians may not have been aware of the other's prescription to the customer or that the customer's symptoms include both cheilitis and herpes zoster. Where a combination of prescriptions from different healthcare professionals may indicate a previously undiagnosed disease, the method 200 may also send a message to the healthcare professional at block 203. The message may include information such as dates of the various prescriptions and/or other customer OTC purchases, dosage and frequency, as well as physician instructions, physicians' contact information, etc. Of course, the same interpolation technique may be used with OTC purchases or any combination of OTC and prescription purchases.

At block 204, the method 200 may compare the disease state progression data 197 to health history data 195H, wherein the health history data 195H was voluntarily provided by the customer, or the health history data 195H was interpolated and/or supplemented by the method at block 203. In some embodiments, the method 200 may compare one or more of a disease or condition name, a stage 197A, and conditions or symptoms 197B of the progression data 197 to the health history data 195H. The method 200 may then determine if the comparison of block 204 produced a match (block 206). A match may include any indication from the comparison of block 204 that the customer is suffering from a disease, undergoing treatment in a rehabilitation or other health care plan, or participating in a regimen that includes one or more of progression states 197A, conditions or symptoms 197B, and time period data 197C. In some embodiments, the comparison of block 204 may determine if any combination of the data within a disease state progression 197 matches the health history data 195H described above. If there is a match, then at block 208, certain health care products 198 associated with any combination of progression states 197A, conditions or symptoms 197B, and time period data 197C may be marketed to the customer by sending marketing information 198C to that customer. For example, the health history data 195H may include data indicating that the customer has been diagnosed with an HIV infection and is suffering from herpes zoster and angular cheilitis. Marketing data 198C related to products that are known to treat herpes zoster and angular cheilitis may then be sent to the customer. Additionally, and with reference to the disease state progression of FIG. 1D, the conditions herpes zoster and angular cheilitis may indicate clinical stage 2 of an HIV infection. Clinical stage 2 of an HIV infection includes many other conditions or symptoms such as recurrent respiratory tract infections and fungal finger nail infections. While the customer's health history data 195H may or may not include specific indications of any other conditions or symptoms associated with clinical stage 2 (e.g., recurrent respiratory tract infections and fungal finger nail infections), the method may anticipate the customer's disease state progression and send marketing data 198C corresponding to products known to treat any other conditions that are likely to occur during clinical stage 2 in combination with the conditions the customer currently exhibits.

As described above in relation to FIG. 10, the matching and marketing of blocks 204, 206, and 208 may be aided by assigning a "tag" or other indication 198B to each product 198A of a listing of healthcare products 198. Continuing with the previous example, a customer exhibiting conditions associated with clinical stage 2 of an HIV infection may benefit from increased product knowledge about products known to treat conditions associated with that disease state. For example, with reference to the disease state progression (e.g., "A") of FIG. 10, a clinical stage 197A (e.g., "2") may include one or more conditions (e.g., "a" and "b"). A healthcare product 198A of the healthcare products listing 198 may include a tag 198B indicating one or more of a disease (e.g., "A"), a clinical stage (e.g., "2") and a condition (e.g., "a" or "b"). If the customer exhibits conditions associated with disease "A" and clinical stage "2", then the method may send marketing data 198C corresponding to certain healthcare products 198A from the products listing 198 that include a tag 198B of either "A2a" or "A2b." As previously described, the customer may or may not actually exhibit conditions "a" or "b" to receive marking data 198C associated with products including the "A2a" and "A2b" tag 198B (e.g., Product 3, Product 5, and Product 6). Rather, blocks 204, 206, and 208 merely need to determine whether or not the customer's disease has progressed to the point that he or she might likely exhibit such conditions. Such likelihood may be determined at block 204 by a variety of comparisons including: comparing a date of various diagnoses related to the disease to a time period that the patient is likely to exhibit various other conditions in a typical disease state progression; comparing a known, diagnosed condition to other conditions that are typical in a known stage of the disease state progression; assigning a likelihood that an exhibited or diagnosed condition will develop into an as yet not exhibited or undiagnosed condition; etc.

In further embodiments, the customer's health history data 195H may include a date associated with a disease diagnosis, a surgery, an injury, or other health condition. Where the health information 195H also includes date information, the method 200 may send marketing data 198C corresponding to healthcare products to the customer based on the likely progression of the customer's condition. Continuing with the previous example, and with reference to the disease state progression 197 of FIG. 1D, if the customer was initially diagnosed with a primary HIV infection on Jul. 10, 2007, the customer may have a higher likelihood of suffering from persistent generalized lymphadenopathy after a given time period from the date of initial diagnosis (e.g., 12 months or on or about Jul. 10, 2008). Thus, at block 208, the method 200 may begin to send marketing data 198C corresponding to healthcare products that are known to treat persistent generalized lymphadenopathy on or about Jul. 10, 2008.

In some embodiments, sending marketing data 198C that matches healthcare products 198A to the customer (as described above in relation to block 208) may include any method of communicating information related to the healthcare products to the customer. The marketing information may be received by the customer via any known data transmission techniques including electronic data transmission techniques that employ TCP/IP, and other methods. For example, marketing data 198C may include personalized ad spaces on a website that is customized for disease state progression marketing as herein described. Such a personalized website may include one or more areas that are communicatively connected to the disease state progression marketing system 100 to display healthcare product information that matches the customer's actual or predicted disease state. The website may be displayed on a display of a web-enabled computing device 114 (FIG. 1). In other embodiments, the marketing data 198C may be e-mailed to the customer, or may cause a flyer or other printed matter to be sent to the customer using regular mail.

Of course, disease state progressions generally present an average disease progression given typical customers and large sample groups of customers with a particular disease. While an average customer diagnosed with an HIV infection may exhibit conditions associated with persistent generalized lymphadenopathy about 12 months after the diagnosis, many customers with similar diagnoses may exhibit such conditions in an earlier or later time period, or not at all. Because individual customers may not progress at the same rate as the average customers used to formulate a disease state progression, adjustments in the marketing generally described by block 208 may need to be made. At block 210, the method may determine if the customer is exhibiting a particular clinical stage 197A or conditions or symptoms 197B that do not follow the average time period 197C of the disease state progression 197. If so, the method 200 may determine a correction factor for the customer at block 212. The correction factor determined at block 212 may be added to the customer's health history data 195H or any other data of the database 146, 182 and may then be used to predict conditions that the customer may exhibit given the customer's individual, rather than typical, progression of a disease, post-op rehab program, or other regimen.

The system and method for disease state marketing may generally contribute to the care and treatment of customers that are suffering from a disease, recovering from injury or operation, or have entered a healthcare regimen that progresses in a known or typical manner. As described herein, the system and method may use the customer's health history information to find products that treat conditions that the customer currently exhibits. Further, the system and method may compare a disease state progression to communicate marketing information to customers regarding conditions they may not currently exhibit, but that other customers with the same or similar conditions have been known to exhibit. Thus, the system and method for disease state marketing may play a significant role in the care and treatment of diseases or scheduled healthcare regimens that progress in a known manner.

This detailed description is to be construed as exemplary only and does not describe every possible embodiment, as describing every possible embodiment would be impractical, if not impossible. One could implement numerous alternate embodiments, using either current technology or technology developed after the filing date of this provisional patent application.

We claim:

1. A disease state progression marketing system configured to transmit healthcare product marketing information to a web-enabled computing device based on a presumed disease state of a customer, the system comprising:

a program memory;

a processor; and a pharmacy database including:
a disease state progression table including one or more disease records, each disease record including a disease having a plurality of disease states, each disease state including a plurality of disease state symptoms presumptive of at least one disease state;
a healthcare product table including marketing data and a marketing data tag corresponding to the marketing data, the marketing data including multimedia information to market a healthcare product to the customer, the marketing data tag including one or more elements describing a relationship between the marketing data and a disease state or at least one disease state symptom;
a plurality of customer records, at least a portion of the plurality of customer records including health history data, the health history data corresponding to one or more health history symptoms presumptive of at least one disease including at least one disease state;
wherein the program memory includes a disease state progression marketing engine including instructions that are executable by the processor to:
compare a customer health history to the disease state progression table;
determine a disease, a disease state, and a disease symptom for a customer based on the comparison of the health history to the disease state progression table;
determine a plurality of marketing data tags including at least the determined disease and disease state;
match the determined marketing data tags to the marketing data, wherein the matched marketing data includes multimedia information to market a healthcare product to the customer to treat disease symptoms for one or more of the determined disease and disease state; and
transmit the marketing data corresponding to the matched marketing data tags to the web-enabled computing device.

2. The disease state progression marketing system of claim 1, wherein at least a portion of the plurality of customer records includes purchase history data, the purchase history data including one or more healthcare products.

3. The disease state progression marketing system of claim 1, wherein the healthcare product is a prescription drug.

4. The disease state progression marketing system of claim 2, wherein the disease state progression marketing engine further includes instructions that are executable by the processor to match each tag corresponding to the marketing data to one or more healthcare products of the purchase history data.

5. The disease state progression marketing system of claim 3, wherein the disease state progression marketing engine further includes instructions that are executable by the processor to determine a disease state based on one or more matched marketing data tags corresponding to the marketing data of one or more healthcare products of the purchase history data.

6. The disease state progression marketing system of claim 1, wherein the disease state progression marketing engine further includes instructions that are executable by the processor to display the transmitted marketing data.

7. The disease state progression marketing system of claim 1, wherein the health history data includes one or more of a disease, a date of disease diagnosis, a date of symptom exhibition, a date of injury, a date of an operation, a disease state, a probable disease state, or a symptom, and the disease state progression marketing engine further includes instructions that are executable by the processor to:
compare the date of a diagnosis to a current date; and
determine a likely disease state using the comparison of the date of the diagnosis to the current date.

8. The disease state progression marketing system of claim 7, wherein the disease state progression marketing engine further includes instructions that are executable by the processor to match a marketing data tag corresponding to the marketing data to each symptom of the determined likely disease state.

9. The disease state progression marketing system of claim 7, wherein the disease state progression marketing engine further includes instructions that are executable by the processor to:
determine a correction factor based on the comparison of the date of the diagnosis to the current date; and
predict the disease state based on the correction factor.

10. The disease state progression marketing system of claim 1, wherein the disease state progression marketing engine further includes instructions that are executable by the processor to match the tag corresponding to the marketing data to each disease state.

11. A computer-implemented method for marketing healthcare products to a customer based on a presumed disease state of a customer via a computer network using a web-enabled computing device, the method comprising:
receiving data at a facility server via the computer network, the data including disease state progression data, healthcare product data, customer data and marketing data tags;
storing the received data in one or more databases that are communicatively linked to the facility server, wherein the disease state progression data includes a disease having a plurality of disease states, each disease state including a plurality of disease state symptoms presumptive of at least one disease state, the healthcare product data including marketing data and a marketing data tag corresponding to the marketing data, the marketing data including multimedia information to market a healthcare product to the customer, the marketing data tag including one or more elements describing a relationship between the marketing data and a disease record state or at least one disease state symptom, and prescription data, the prescription data corresponding to one or more disease state symptoms;
causing a processor of the facility server to:
compare a customer health history to the disease state progression data;
determine a disease, a disease state, and a disease symptom for a customer based on the comparison of the customer health history to the disease state progression data;
determine one or more marketing data tags including at least the determined disease and disease state;
match the determined marketing data tags to the marketing data, wherein the matched marketing data includes multimedia information to market a healthcare product to the customer to treat disease symptoms for one or more of the determined disease and disease state; and
transmitting the marketing data corresponding to the matched marketing data tags from the facility server to the web-enabled computing device via the computer network.

12. The method of claim 11, wherein the customer data includes purchase history data, the purchase history data including one or more healthcare products, the method further comprising:

causing the processor of the facility server to match each marketing data tag to one or more healthcare products of the purchase history data, and causing the processor of the facility server to determine a disease state based on one or more matched marketing data tags of one or more healthcare products of the purchase history data.

13. The method of claim 11, further comprising causing a processor of the web-enabled computing device to display the transmitted marketing data.

14. The method of claim 11, wherein the customer data includes one or more of a disease, a date of disease diagnosis, a date of symptom exhibition, a date of injury, a date of an operation, a disease state, a probable disease state, or a symptom.

15. The method of claim 14, further comprising:

causing the processor of the facility server to compare the date of a diagnosis to a current date;

causing the processor of the facility server to determine a likely disease state using the comparison of the date of the diagnosis to the current date; and causing the processor of the facility server to match a tag corresponding to the marketing data to each symptom of the determined likely disease state.

16. The method of claim 15, further comprising:

causing the processor of the facility server to determine a correction factor based on the comparison of the date of the diagnosis to the current date; and causing the processor of the facility server to predict the disease state based on the correction factor.

17. A computer readable storage medium comprising computer executable instructions to market healthcare products to a customer using a web-enabled computing device based on a presumed disease state of a customer, the instructions comprising:

receiving data at a facility server via the computer network, the data including disease state progression data, healthcare product data, customer data and marketing data tags;

storing the received data, wherein the disease state progression data including includes a disease having a plurality of disease states, each disease state including a plurality of disease state symptoms presumptive of at least one disease state, the healthcare product data including marketing data and a marketing data tag corresponding to the marketing data, the marketing data including multimedia information to market a healthcare product to the customer, the marketing data tag including one or more elements describing a relationship between the marketing data and a disease state or at least one disease state symptom, and the customer data includes health history data and purchase history data, the health history data corresponding to one or more health history symptoms presumptive of at least one disease and disease state, a date of disease diagnosis, a date of symptom exhibition, a date of injury, a date of an operation, or a probable disease state, the purchase history data including one or more healthcare products;

comparing the customer health history data to the disease state progression data;

determining a disease, a disease state, and a disease symptom for a customer based on the comparison of the customer health history to the disease state progression data;

determine one or more marketing data tags including at least the determined disease and disease state;

matching the determined marketing data tags to the marketing data, wherein the matched marketing data includes multimedia information to market a healthcare product to the customer to treat disease symptoms for one or more of the determined disease and disease state; and electronically transmitting the marketing data corresponding to the matched marketing data tags from the facility server to the web-enabled computing device.

18. The computer readable storage medium of claim 17, wherein the instructions further comprise:

comparing the date of a diagnosis to a current date; and determining the probable disease state using the comparison of the date of the diagnosis to the current date.

19. The computer readable storage medium of claim 18, wherein the instructions further comprise:

determining a correction factor based on the comparison of the date of the diagnosis to the current date; and predicting the disease state based on the correction factor.

\* \* \* \* \*